US007386152B2

(12) United States Patent
Rowe et al.

(10) Patent No.: US 7,386,152 B2
(45) Date of Patent: *Jun. 10, 2008

(54) NONINVASIVE ALCOHOL SENSOR

(75) Inventors: Robert K. Rowe, Corrales, NM (US);
Robert M. Harbour, Santa Fe, NM (US)

(73) Assignee: Lumidigm, Inc., Albuquerque, NM (US)

( * ) Notice: Subject to any disclaimer, the term of this patent is extended or adjusted under 35 U.S.C. 154(b) by 90 days.

This patent is subject to a terminal disclaimer.

(21) Appl. No.: 11/178,066

(22) Filed: Jul. 8, 2005

(65) Prior Publication Data

US 2006/0002598 A1 Jan. 5, 2006

Related U.S. Application Data

(63) Continuation of application No. 10/818,698, filed on Apr. 5, 2004, now Pat. No. 7,147,153.

(60) Provisional application No. 60/552,662, filed on Mar. 10, 2004, provisional application No. 60/504,594, filed on Sep. 18, 2003, provisional application No. 60/483,281, filed on Jun. 27, 2003, provisional application No. 60/460,247, filed on Apr. 4, 2003.

(51) Int. Cl.
*G06K 9/00* (2006.01)

(52) U.S. Cl. ............ 382/124; 382/115; 340/5.53; 340/5.83

(58) Field of Classification Search ........... 382/115, 382/124; 340/5.53, 5.83
See application file for complete search history.

(56) References Cited

U.S. PATENT DOCUMENTS

| 3,508,830 | A | | 4/1970 | Hopkins et al. | |
|---|---|---|---|---|---|
| 3,854,319 | A | * | 12/1974 | Burroughs et al. | 73/1.03 |
| 3,910,701 | A | | 10/1975 | Henderson et al. | |
| RE29,008 | E | | 10/1976 | Ott | |
| 4,035,083 | A | | 7/1977 | Woodriff et al. | |
| 4,142,797 | A | | 3/1979 | Astheimer | |
| 4,169,676 | A | | 10/1979 | Kaiser | |

(Continued)

FOREIGN PATENT DOCUMENTS

EP      0 280 418 A1     8/1988

(Continued)

OTHER PUBLICATIONS

Zavala, Albert & Paley, James J. "Using fingerprint measures to predict other anthropometric Variables" Human Factors, 1975, pp. 591-602, vol. 17, No. 6.

(Continued)

*Primary Examiner*—Bhavesh M. Mehta
*Assistant Examiner*—John B Strege
(74) *Attorney, Agent, or Firm*—Townsend and Townsend and Crew LLP

(57) ABSTRACT

Methods and systems are provided for biometric sensing. An illumination subsystem provides light at discrete wavelengths to a skin site of an individual. A detection subsystem receives light scattered from the skin site. A computational unit is interfaced with the detection system. The computational unit has instructions for deriving a spatially distributed multispectral image from the received light at the discrete wavelengths. The computational unit also has instructions for comparing the derived multispectral image with a database of multispectral images to identify the individual.

39 Claims, 7 Drawing Sheets

U.S. PATENT DOCUMENTS

| | | |
|---|---|---|
| 4,260,220 A | 4/1981 | Whitehead |
| 4,322,163 A | 3/1982 | Schiller |
| 4,427,889 A | 1/1984 | Muller |
| 4,537,484 A | 8/1985 | Fowler et al. |
| 4,598,715 A | 7/1986 | Machler et al. |
| 4,653,880 A | 3/1987 | Sting et al. |
| 4,654,530 A | 3/1987 | Dybwad |
| 4,655,225 A | 4/1987 | Dahne et al. |
| 4,656,562 A | 4/1987 | Sugino |
| 4,657,397 A | 4/1987 | Oehler et al. |
| 4,661,706 A | 4/1987 | Messerschmidt et al. |
| 4,684,255 A | 8/1987 | Ford |
| 4,712,912 A | 12/1987 | Messerschmidt |
| 4,730,882 A | 3/1988 | Messerschmidt |
| 4,747,147 A | 5/1988 | Sparrow |
| 4,787,013 A | 11/1988 | Sugino et al. |
| 4,787,708 A | 11/1988 | Whitehead |
| 4,830,496 A | 5/1989 | Young |
| 4,853,542 A | 8/1989 | Milosevic et al. |
| 4,857,735 A | 8/1989 | Noller |
| 4,859,064 A | 8/1989 | Messerschmidt et al. |
| 4,866,644 A | 9/1989 | Shenk et al. |
| 4,867,557 A | 9/1989 | Takatani et al. |
| 4,882,492 A | 11/1989 | Schlager |
| 4,883,953 A | 11/1989 | Koashi et al. |
| 4,936,680 A | 6/1990 | Henkes et al. |
| 4,944,021 A | 7/1990 | Hoshino et al. |
| 4,975,581 A | 12/1990 | Robinson et al. |
| 5,015,100 A | 5/1991 | Doyle |
| 5,019,715 A | 5/1991 | Sting et al. |
| 5,028,787 A | 7/1991 | Rosenthal et al. |
| 5,051,602 A | 9/1991 | Sting et al. |
| 5,055,658 A * | 10/1991 | Cockburn .................. 235/382 |
| 5,068,536 A | 11/1991 | Rosenthal |
| 5,070,874 A | 12/1991 | Barnes et al. |
| 5,077,803 A | 12/1991 | Kato et al. |
| 5,146,102 A | 9/1992 | Higuchi et al. |
| 5,158,082 A | 10/1992 | Jones |
| 5,163,094 A | 11/1992 | Prokoski et al. |
| 5,178,142 A | 1/1993 | Harjunmaa et al. |
| 5,179,951 A | 1/1993 | Knudson |
| 5,204,532 A | 4/1993 | Rosenthal |
| 5,222,495 A | 6/1993 | Clarke et al. |
| 5,222,496 A | 6/1993 | Clarke et al. |
| 5,223,715 A | 6/1993 | Taylor |
| 5,225,678 A | 7/1993 | Messerschmidt |
| 5,230,702 A | 7/1993 | Lindsay et al. |
| 5,237,178 A | 8/1993 | Rosenthal et al. |
| 5,243,546 A | 9/1993 | Maggard |
| 5,257,086 A | 10/1993 | Fateley et al. |
| 5,258,922 A | 11/1993 | Grill |
| 5,267,152 A | 11/1993 | Yang et al. |
| 5,268,749 A | 12/1993 | Weber et al. |
| 5,291,560 A | 3/1994 | Daugman |
| 5,299,570 A | 4/1994 | Hatschek |
| 5,303,026 A | 4/1994 | Strobl et al. |
| 5,311,021 A | 5/1994 | Messerschmidt |
| 5,313,941 A | 5/1994 | Braig et al. |
| 5,321,265 A | 6/1994 | Block |
| 5,331,958 A | 7/1994 | Oppenheimer |
| 5,348,003 A | 9/1994 | Caro |
| 5,351,686 A | 10/1994 | Steuer et al. |
| 5,355,880 A | 10/1994 | Thomas et al. |
| 5,360,004 A | 11/1994 | Purdy et al. |
| 5,361,758 A | 11/1994 | Hall et al. |
| 5,366,903 A | 11/1994 | Lundsgaard et al. |
| 5,372,135 A | 12/1994 | Mendelson et al. |
| 5,379,764 A | 1/1995 | Barnes et al. |
| 5,402,778 A | 4/1995 | Chance |
| 5,405,315 A | 4/1995 | Khuri et al. |
| 5,419,321 A | 5/1995 | Evans |
| 5,435,309 A | 7/1995 | Thomas et al. |
| 5,441,053 A | 8/1995 | Lodder et al. |
| 5,452,723 A | 9/1995 | Wu et al. |
| 5,459,317 A | 10/1995 | Small et al. |
| 5,459,677 A | 10/1995 | Kowalski et al. |
| 5,460,177 A | 10/1995 | Purdy et al. |
| 5,483,335 A | 1/1996 | Tobias |
| 5,494,032 A | 2/1996 | Robinson et al. |
| 5,505,726 A | 4/1996 | Meserol |
| 5,507,723 A | 4/1996 | Keshaviah |
| 5,515,847 A | 5/1996 | Braig et al. |
| 5,518,623 A | 5/1996 | Keshaviah et al. |
| 5,523,054 A | 6/1996 | Switalski et al. |
| 5,533,509 A | 7/1996 | Koashi et al. |
| 5,537,208 A | 7/1996 | Bertram et al. |
| 5,539,207 A | 7/1996 | Wong et al. |
| 5,552,997 A | 9/1996 | Massart |
| 5,559,504 A | 9/1996 | Itsumi et al. |
| 5,568,251 A | 10/1996 | Davies et al. |
| 5,596,992 A | 1/1997 | Haaland et al. |
| 5,606,164 A | 2/1997 | Price et al. |
| 5,630,413 A | 5/1997 | Thomas et al. |
| 5,636,633 A | 6/1997 | Messerschmidt et al. |
| 5,655,530 A | 8/1997 | Messerschmidt |
| 5,672,864 A | 9/1997 | Kaplan |
| 5,672,875 A | 9/1997 | Block et al. |
| 5,677,762 A | 10/1997 | Ortyn et al. |
| 5,681,273 A | 10/1997 | Brown |
| 5,708,593 A | 1/1998 | Saby et al. |
| 5,719,399 A | 2/1998 | Alfano et al. |
| 5,719,950 A | 2/1998 | Osten et al. |
| 5,724,268 A | 3/1998 | Sodickson et al. |
| 5,729,619 A * | 3/1998 | Puma .......................... 382/115 |
| 5,737,439 A | 4/1998 | Lapsley et al. |
| 5,743,262 A | 4/1998 | Lepper, Jr. et al. |
| 5,747,806 A | 5/1998 | Khalil |
| 5,750,994 A | 5/1998 | Schlager |
| 5,751,835 A | 5/1998 | Topping et al. |
| 5,761,330 A | 6/1998 | Stoianov et al. |
| 5,782,755 A | 7/1998 | Chance et al. |
| 5,792,050 A | 8/1998 | Alam et al. |
| 5,792,053 A | 8/1998 | Skladnev et al. |
| 5,793,881 A | 8/1998 | Stiver et al. |
| 5,796,858 A | 8/1998 | Zhou et al. |
| 5,808,739 A | 9/1998 | Turner et al. |
| 5,818,048 A | 10/1998 | Sodickson et al. |
| 5,823,951 A | 10/1998 | Messerschmidt et al. |
| 5,828,066 A | 10/1998 | Messerschmidt |
| 5,830,132 A | 11/1998 | Robinson |
| 5,830,133 A | 11/1998 | Osten et al. |
| 5,850,623 A | 12/1998 | Carman, Jr. et al. |
| 5,853,370 A | 12/1998 | Chance et al. |
| 5,857,462 A * | 1/1999 | Thomas et al. ............. 600/310 |
| 5,860,421 A | 1/1999 | Eppstein et al. |
| 5,867,265 A | 2/1999 | Thomas |
| 5,886,347 A | 3/1999 | Inoue et al. |
| 5,902,033 A | 5/1999 | Levis et al. |
| 5,914,780 A | 6/1999 | Turner et al. |
| 5,929,443 A | 7/1999 | Alfano et al. |
| 5,933,792 A | 8/1999 | Andersen et al. |
| 5,935,062 A | 8/1999 | Messerschmidt et al. |
| 5,945,676 A | 8/1999 | Khalil |
| 5,949,543 A | 9/1999 | Bleier et al. |
| 5,957,841 A | 9/1999 | Maruo et al. |
| 5,961,449 A | 10/1999 | Toida et al. |
| 5,963,319 A | 10/1999 | Jarvis et al. |
| 5,987,346 A | 11/1999 | Benaron et al. |
| 5,999,637 A | 12/1999 | Toyoda et al. |
| 6,005,722 A | 12/1999 | Butterworth et al. |
| 6,016,435 A | 1/2000 | Maruo et al. |
| 6,025,597 A | 2/2000 | Sterling et al. |
| 6,026,314 A * | 2/2000 | Amerov et al. ............. 600/322 |
| 6,028,773 A | 2/2000 | Hundt |

| | | | |
|---|---|---|---|
| 6,031,609 A | 2/2000 | Funk et al. | |
| 6,034,370 A | 3/2000 | Messerschmidt | |
| 6,040,578 A | 3/2000 | Malin et al. | |
| 6,041,247 A | 3/2000 | Weckstrom et al. | |
| 6,041,410 A * | 3/2000 | Hsu et al. | 713/186 |
| 6,043,492 A | 3/2000 | Lee et al. | |
| 6,044,285 A | 3/2000 | Chaiken et al. | |
| 6,045,502 A | 4/2000 | Eppstein et al. | |
| 6,046,808 A | 4/2000 | Fateley | |
| 6,049,727 A | 4/2000 | Crothall | |
| 6,056,738 A | 5/2000 | Marchitto et al. | |
| 6,057,925 A | 5/2000 | Anthon | |
| 6,061,581 A | 5/2000 | Alam et al. | |
| 6,061,582 A | 5/2000 | Small et al. | |
| 6,066,847 A | 5/2000 | Rosenthal | |
| 6,069,689 A | 5/2000 | Zeng et al. | |
| 6,070,093 A * | 5/2000 | Oosta et al. | 600/316 |
| 6,073,037 A | 6/2000 | Alam et al. | |
| 6,088,605 A | 7/2000 | Griffith et al. | |
| 6,088,607 A | 7/2000 | Diab et al. | |
| 6,097,035 A | 8/2000 | Belongie et al. | |
| 6,100,811 A | 8/2000 | Hsu et al. | |
| 6,115,484 A | 9/2000 | Bowker et al. | |
| 6,115,673 A | 9/2000 | Malin et al. | |
| 6,122,042 A * | 9/2000 | Wunderman et al. | 356/73 |
| 6,122,394 A | 9/2000 | Neukermans et al. | |
| 6,122,737 A | 9/2000 | Bjorn et al. | |
| 6,125,192 A | 9/2000 | Björn et al. | |
| 6,141,101 A | 10/2000 | Bleier et al. | |
| 6,147,749 A | 11/2000 | Kubo et al. | |
| 6,148,094 A | 11/2000 | Kinsella | |
| 6,152,876 A | 11/2000 | Robinson et al. | |
| 6,154,658 A | 11/2000 | Caci | |
| 6,157,041 A | 12/2000 | Thomas et al. | |
| 6,159,147 A | 12/2000 | Lichter et al. | |
| 6,172,743 B1 | 1/2001 | Kley et al. | |
| 6,175,407 B1 | 1/2001 | Sartor | |
| 6,181,414 B1 | 1/2001 | Raz et al. | |
| 6,181,958 B1 | 1/2001 | Steuer et al. | |
| 6,188,781 B1 | 2/2001 | Brownlee | |
| 6,212,424 B1 | 4/2001 | Robinson | |
| 6,226,541 B1 | 5/2001 | Eppstein et al. | |
| 6,229,908 B1 * | 5/2001 | Edmonds et al. | 382/124 |
| 6,230,034 B1 | 5/2001 | Messerschmidt et al. | |
| 6,236,047 B1 * | 5/2001 | Malin et al. | 250/339.12 |
| 6,240,306 B1 | 5/2001 | Rohrscheib et al. | |
| 6,240,309 B1 | 5/2001 | Yamashita et al. | |
| 6,241,663 B1 | 6/2001 | Wu et al. | |
| 6,256,523 B1 | 7/2001 | Diab et al. | |
| 6,272,367 B1 | 8/2001 | Chance | |
| 6,280,381 B1 | 8/2001 | Malin et al. | |
| 6,282,303 B1 | 8/2001 | Brownlee | |
| 6,285,895 B1 | 9/2001 | Ristolainen et al. | |
| 6,292,576 B1 | 9/2001 | Brownlee | |
| 6,301,815 B1 | 10/2001 | Sliwa | |
| 6,304,767 B1 | 10/2001 | Soller et al. | |
| 6,307,633 B1 | 10/2001 | Mandella et al. | |
| 6,309,884 B1 | 10/2001 | Cooper et al. | |
| 6,317,507 B1 | 11/2001 | Dolfing et al. | |
| 6,324,310 B1 | 11/2001 | Brownlee | |
| 6,330,346 B1 | 12/2001 | Peterson et al. | |
| 6,404,904 B1 | 6/2002 | Einighammer et al. | |
| 6,419,361 B2 * | 7/2002 | Cabib et al. | 351/221 |
| 6,483,929 B1 | 11/2002 | Murakami et al. | |
| 6,504,614 B1 | 1/2003 | Messerschmidt et al. | |
| 6,537,225 B1 | 3/2003 | Mills | |
| 6,560,352 B2 | 5/2003 | Rowe et al. | |
| 6,574,490 B2 | 6/2003 | Abbink et al. | |
| 6,606,509 B2 | 8/2003 | Schmitt | |
| 6,628,809 B1 | 9/2003 | Rowe et al. | |
| 6,741,729 B2 | 5/2004 | Bjorn et al. | |
| 6,799,275 B1 | 9/2004 | Bjorn | |
| 6,816,605 B2 | 11/2004 | Rowe et al. | |
| 7,147,153 B2 * | 12/2006 | Rowe et al. | 235/382 |
| 2002/0171834 A1 | 11/2002 | Rowe et al. | |
| 2002/0183624 A1 * | 12/2002 | Rowe et al. | 600/476 |
| 2003/0044051 A1 | 3/2003 | Fujieda | |
| 2003/0078504 A1 | 4/2003 | Rowe et al. | |
| 2004/0008875 A1 | 1/2004 | Linares | |
| 2004/0047493 A1 | 3/2004 | Rowe et al. | |
| 2004/0240712 A1 | 12/2004 | Rowe et al. | |
| 2005/0007582 A1 | 1/2005 | Villers et al. | |
| 2005/0185857 A1 | 8/2005 | Rowe | |
| 2005/0205667 A1 | 9/2005 | Rowe | |

FOREIGN PATENT DOCUMENTS

| | | |
|---|---|---|
| EP | 0 897 164 A2 | 2/1999 |
| EP | 0 924 656 A2 | 6/1999 |
| EP | 1434162 A2 | 6/2004 |
| JP | 2001184490 A | 7/2001 |
| JP | 2002133402 A | 5/2002 |
| JP | 2003308520 A | 10/2003 |
| WO | WO 92/17765 A1 | 10/1992 |
| WO | WO 93/07801 A1 | 4/1993 |
| WO | WO 9307801 A1 * | 4/1993 |
| WO | WO 01/18332 A1 | 3/2001 |
| WO | WO 01/27882 A2 | 4/2001 |
| WO | WO 01/52180 A1 | 7/2001 |
| WO | WO 01/52726 A1 | 7/2001 |
| WO | WO 01/53805 A1 | 7/2001 |
| WO | WO 02/084605 A2 | 10/2002 |
| WO | WO 02/099393 A2 | 12/2002 |
| WO | WO 2004/068388 A2 | 8/2004 |
| WO | WO 2004/068394 A1 | 8/2004 |

OTHER PUBLICATIONS

Bantle, John P. & Thomas, William, "Glucose Measurement in Patients with Diabetes Mellitus with Dermal Interstitial Fluid," Copyright © 1997 by Mosby-Year Book, Inc., 9 pages.

Berkoben et al., "Vascular Access for Hemodialysis", Clinical Dialysis, published on or before Oct. 30, 1997, 20 pages.

Bleyer et al., "The costs of Hospitalizations Due to Hemodialysis Access Management", Nephrology News & Issues, Jan. 1995, pp. 19, 20 and 22.

Brochure entitled "Determination of Delivered Therapy Through Measurement of Effective Clearance", Feresenius USA, Dec. 1994, 1 page.

Daugirdas et al., "Comparison of Methods to Predict the Equilibrated Kt/V (eKt/V) in the Hemo Study", National Institutes of Health, NIDDK, Bethesda, MD, Aug. 20, 1996.

Depner et al., "Clinical Measurement of Blood Flow in Hemodialysis Access Fistulae and Grafts by Ultrasound Dilution", from the Department of Nephrology, University of California, published bon or before Oct. 30, 1997, 4 pages.

Hakim et al., "Effects of Dose of Dialysis on Morbidity and Mortality", American Journal of Kidney Diseases, vol. 23, No. 5, May 1994, pp. 661-669.

Jacobs, et al., "A Disposable Urea Sensor for Continuous Monitoring of Hemodialysis Efficiency", USAIO Journal, 1993, pp. M353-M358.

Keshaviah et al., "On-line monitoring of the delivery of the hemodialysis prescription", Pediatric Nephrology, vol. 9, 1995, pp. S2-S8.

Krivitski, "Theory and Validation of Access Flow Measurement by Dilution Technique During Hemodialysis", Kidney International, vol. 48, 1995, pp. 244-250.

Marbach, Ralf, "Measurement Techniques for IR Spectroscopic Blood Glucose Determination," (1994) pp. 1-158.

Mardia, K.V. et al., Multivariate Analysis, Academic Press (1979) pp. 300-325.

Nichols, et al., "Design and Testing of a White-Light, Steady-State Diffuse Reflectance Spectrometer for Determination of Optical Properties of Highly Scattering Systems," Applied Optics, Jan. 1, 1997, 36(1), pp. 93-104.

Ripley, B.D., Pattern Recognition and Neural Networks, Cambridge University Press (1996) pp. 91-120.

Ronco et al., "On-line urea monitoring: a further step towards adequate dialysis prescription and delivery", Int'l. Journal of Artificial Organs, vol. 18, No. 9, 1995, pp. 534-543.

Service, F. John et al., "Dermal Interstitial Glucose as an Indicator of Ambient Glycemia," Diabetes Care, vol. 20, No. 9, Sep. 1997, 9 pages.

Sherman, "Recirculation in the Hemodialysis Access", Principles and Practice of Dialysis, 1994, pp. 38-46.

Sherman, "The Measurement of Dialysis Access Recirculation", American Journal of Kidney Diseases, vol. 22, No. 4, Oct. 1993, pp. 616-621.

Steuer et al., "A New Optical Technique for Monitoring Hematocrit and Circulating Blood Volume: Its Application in Renal Dialysis", Dialysis & Transplantation, vol. 22, No. 5, May 1993, pp. 260-265.

Webb, Paul, "Temperatures of Skin, Subcutaneous Tissue, Muscle and Core in Resting Men in Cold, Comfortable and Hot Conditions," European Journal of Applied Physiology, vol. 64 (1992) pp. 471-476.

Demos, S.G. & Alfano R.R. "Optical fingerprinting using polarisation contrast improvement" Electronics Letters, Mar. 27, 1997, pp. 582-584, vol. 33, No. 7.

\* cited by examiner 400 nm Illumination    500 nm Illumination    600 nm Illumination

NONINVASIVE ALCOHOL SENSOR

CROSS-REFERENCES TO RELATED APPLICATIONS

This application is a continuation of U.S. patent application Ser. No. 10/818,698, entitled "MULTISPECTRAL BIOMETRIC SENSOR," filed Apr. 5, 2004 now U.S. Pat. No. 7,147,153 by Robert K. Rowe et al. ("the '698 application), the entire disclosure of which is incorporated herein by reference for all purposes. The '698 application is a nonprovisional of, and claims the benefit of the filing date of each of the following provisional applications, the entire disclosure of each of which is incorporated herein by reference for all purposes: U.S. Prov. Pat. Appl. No. 60/460,247, entitled "NONINVASIVE ALCOHOL MONITOR," filed Apr. 4, 2003; U.S. Prov. Pat. Appl. No. 60/483,281, entitled "HYPERSPECTRAL FINGERPRINT READER," filed Jun. 27, 2003 by Robert K. Rowe et al.; U.S. Prov. Pat. Appl. No. 60/504,594, entitled "HYPERSPECTRAL FINGERPRINTING," filed Sep. 18, 2003; and U.S. Prov. Pat. Appl. No. 60/552,662, entitled "OPTICAL SKIN SENSOR FOR BIOMETRICS," filed Mar. 10, 2004.

This application is also related to U.S. patent application Ser. No. 09/874,740, entitled "APPARATUS AND METHOD OF BIOMETRIC DETERMINATION USING SPECIALIZED OPTICAL SPECTROSCOPY SYSTEM," filed Jun. 5, 2001, the entire disclosure of which is incorporated herein by reference for all purposes.

BACKGROUND OF THE INVENTION

This application relates generally to biometrics. More specifically, this application relates to methods and systems for performing biometric measurements with a multispectral imaging sensor, and to methods and systems for measuring in vivo levels of alcohol or other analytes.

"Biometrics" refers generally to the statistical analysis of characteristics of living bodies. One category of biometrics includes "biometric identification," which commonly operates under one of two modes to provide automatic identification of people or to verify purported identities of people. Biometric sensing technologies measure the physical features or behavioral characteristics of a person and compare those features to similar prerecorded measurements to determine whether there is a match. Physical features that are commonly used for biometric identification include faces, irises, hand geometry, vein structure, and fingerprint patterns, which is the most prevalent of all biometric-identification features. Current methods for analyzing collected fingerprints include optical, capacitive, radio-frequency, thermal, ultrasonic, and several other less common techniques.

Most of the fingerprint-collection methods rely on measuring characteristics of the skin at or very near the surface of a finger. In particular, optical fingerprint readers typically rely on the presence or absence of a difference in the index of refraction between the sensor platen and the finger placed on it. When an air-filled valley of the fingerprint is above a particular location of the platen, total internal reflectance ("TIR") occurs in the platen because of the air-platen index difference. Alternatively, if skin of the proper index of refraction is in optical contact with the platen, then the TIR at this location is "frustrated," allowing light to traverse the platen-skin interface. A map of the differences in TIR across the region where the finger is touching the platen forms the basis for a conventional optical fingerprint reading. There are a number of optical arrangements used to detect this variation of the optical interface in both bright-field and dark-field optical arrangements. Commonly, a single, quasi-monochromatic beam of light is used to perform this TIR-based measurement.

There also exists non-TIR optical fingerprint sensors. In most cases, these sensors rely on some arrangement of quasimonochromatic light to illuminate the front, sides, or back of a fingertip, causing the light to diffuse through the skin. The fingerprint image is formed due to the differences in light transmission across the skin-platen boundary for the ridge and valleys. The difference in optical transmission are due to changes in the Fresnel reflection characteristics due to the presence or absence of any intermediate air gap in the valleys, as known to one of familiarity in the art.

Optical fingerprint readers are particularly susceptible to image quality problems due to non-ideal conditions. If the skin is overly dry, the index match with the platen will be compromised, resulting in poor image contrast. Similarly, if the finger is very wet, the valleys may fill with water, causing an optical coupling to occur all across the fingerprint region and greatly reducing image contrast. Similar effects may occur if the pressure of the finger on the platen is too little or too great, the skin or sensor is dirty, the skin is aged and/or worn, or overly fine features are present such as may be the case for certain ethnic groups and in very young children. These effects decrease image quality and thereby decrease the overall performance of the fingerprint sensor. In some cases, commercial optical fingerprint readers incorporate a thin membrane of soft material such as silicone to help mitigate these effects and restore performance. As a soft material, the membrane is subject to damage, wear, and contamination, limiting the use of the sensor without maintenance.

Biometric sensors, particularly fingerprint biometric sensors, are generally prone to being defeated by various forms of spoof samples. In the case of fingerprint readers, a variety of methods are known in the art for presenting readers with a fingerprint pattern of an authorized user that is embedded in some kind of inanimate material such as paper, gelatin, epoxy, latex, and the like. Thus, even if a fingerprint reader can be considered to reliably determine the presence or absence of a matching fingerprint pattern, it is also critical to the overall system security to ensure that the matching pattern is being acquired from a genuine, living finger, which may be difficult to ascertain with many common sensors.

Another way in which some biometric systems may be defeated is through the use of a replay attack. In this scenario, an intruder records the signals coming from the sensor when an authorized user is using the system. At a later time, the intruder manipulates the sensor system such that the prerecorded authorized signals may be injected into the system, thereby bypassing the sensor itself and gaining access to the system secured by the biometric.

A common approach to making biometric sensors more robust, more secure, and less error-prone is to combine sources of biometric signals using an approach sometimes referred to in the art as using "dual," "combinatoric," "layered," "fused," or "multifactor biometric sensing. To provide enhanced security in this way, biometric technologies are combined in such a way that different technologies measure the same portion of the body at the same time and are resistant to being defeated by using different samples or techniques to defeat the different sensors that are combined.

When technologies are combined in a way that they view the same part of the body they are referred to as being "tightly coupled."

The accuracy of noninvasive optical measurements of physiological analytes such as glucose, alcohol, hemoglobin, urea, and cholesterol can be adversely affected by variation of the skin tissue. In some cases it is advantageous to measure one or more physiological analytes in conjunction with a biometric measurement. Such dual measurement has potential interest and application to both commercial and law-enforcement markets.

There is accordingly a general need in the art for improved methods and systems for biometric sensing and analyte estimation using multispectral imaging systems and methods.

BRIEF SUMMARY OF THE INVENTION

Embodiments of the invention thus provide methods and systems for biometric sensing and physiological analyte estimation. The embodiments of the present invention collect multispectral image data that represent spatio-spectral information from multiple skin features at various depths and positions within an image volume. The information from the different features can be advantageously combined to provide for methods of biometric identification, including identity verification. As well, the multispectral image data may be processed to provide information about the authenticity or liveness state of a sample. The multispectral image data may also be used to ascertain information about the presence and amount of particular physiological analytes that may be present in the tissue at the image location.

Embodiments of the invention provide methods and systems for assessing skin composition and structure in a certain location on the body using optical techniques. When light of a particular wavelength enters the skin, it is subject to optical interactions that include absorbance and scatter. Due to the optical scatter, a portion of the light will generally be diffusely reflected from the skin after entering the skin at the illumination point. An image of the light thus reflected contains information about the portion of the skin that the light passes through while traveling from the point of illumination to detection. Different wavelengths of light will interact with skin differently. Due to the properties of certain skin components, certain wavelengths of light will interact more or less strongly with certain components and structures. As well, certain wavelengths of light will travel greater distances into and through the skin before being scattered back out of the skin and detected. Accurate measurement of the spatial characteristics of light that is diffusely reflected from skin thus contains information about the components and structures in the skin that interacted with light of a certain wavelength. Similar measurements made using light of multiple and different illumination wavelengths provides additional information about the skin composition and structure.

In one set of embodiments, a sensor system is provided. An illumination subsystem is disposed to provide light at a plurality of discrete wavelengths to a skin site of an individual. A detection subsystem is disposed to receive light scattered from the skin site. A computational unit is interfaced with the detection system. The computational unit has instructions for deriving a spatially distributed multispectral image from the received light at the plurality of discrete wavelengths. The computational unit also has instructions for comparing the derived multispectral image with a database of multispectral images to identify the individual.

The identification of the individual may be performed differently in different embodiments. In one embodiment, the instructions for comparing the derived multispectral image with the database comprise instructions for searching the database for an entry identifying a multispectral image consistent with the derived multispectral image. In another embodiment, the instructions for comparing the derived multispectral image with the database comprise instructions for comparing the derived multispectral image with the multispectral image at an entry of the database corresponding to a purported identity of the individual to verify the purported identity.

The illumination subsystem may comprise a light source that provides the light to the plurality of discrete wavelengths, and illumination optics to direct the light to the skin site. In some instances, a scanner mechanism may also be provided to scan the light in a specified pattern. The light source may comprise a plurality of quasimonochromatic light sources, such as LEDs or laser diodes. Alternatively, the light source may comprise a broadband light source, such as an incandescent bulb or glowbar, and a filter disposed to filter light emitted from the broad band source. The filter may comprise a continuously variable filter in one embodiment. In some cases, the detection system may comprise a light detector, an optically dispersive element, and detection optics. The optically dispersive element is disposed to separate wavelength components of the received light, and the detection optics direct the received light to the light detector. In one embodiment, both the illumination and detection subsystems comprise a polarizer. The polarizers may be circular polarizers, linear polarizers, or a combination. In the case of linear polarizers, the polarizers may be substantially crossed relative to each other.

The sensor system may comprise a platen to contact the skin site, or the sensor system may be configured for noncontact operation. The platen may be adapted for the skin site to be swiped over a surface of the platen. In one such embodiment, the platen comprises an optically clear roller that the finger can roll across with a swipe motion. In such an embodiment, the instructions for deriving the spatially distributed multispectral image include instructions for building up the multispectral image from light received from different portions of the skin site as the skin site is rolled.

The illumination subsystem may comprise a plurality of illumination subsystems. In different embodiments, the plurality of discrete wavelengths are provided sequentially or are provided substantially simultaneously and with an identifiable encoding. Suitable wavelengths for the plurality of discrete wavelengths include wavelengths between about 400 nm and 2.5 µm.

In some embodiments, the sensor system may have additional components to allow the estimation of other parameters. For instance, in one embodiment, the computational system further has instructions for deriving spectral-distribution characteristics from the received light. Such spectral-distribution characteristics may be used to determine an analyte concentration in tissue below a surface of the skin site, such as a concentration of alcohol, glucose, hemoglobin, urea, and cholesterol. In another embodiment, the computational system further has instructions for determining a liveness state from the derived spectral-distribution characteristics.

In a second set of embodiments, methods are provided for identifying an individual. A skin site of the individual is illuminated at a plurality of discrete wavelengths. Light scattered from the skin site is received. A spatially distributed multispectral image is derived from the received light at the plurality of discrete wavelengths. The derived multispectral image data or one or more of its parts are compared with a database of derived multispectral images. Various of the embodiments include aspects discussed above in connection with embodiments for the sensor system. In some instances, the methods allow generation of measurement sequences that are not constant for all samples. In one embodiment, a sequence of illumination wavelengths is changed between measurements. In another embodiment, the selection of which illumination wavelengths are used to illuminate the skin are changed between measurements.

In a third set of embodiments, a sensor system is provided. An illumination subsystem is disposed to provide light at a plurality of discrete wavelengths to a sample. A detection subsystem is disposed to receive light scattered within tissue of the sample. A computational unit is interfaced with the detection subsystem. The computational unit has instructions for deriving multispectral characteristics of the received light at the plurality of distinct wavelengths. The computational unit also has instructions for determining a liveness state of the tissue from the derived multispectral characteristics. In one such embodiment, the liveness state is determined by pixelating spatial distributions of the derived multispectral characteristics. An multivariate factor analysis is performed on a matrix having entries in a first dimension corresponding to a pixel of a pixelated spatial distribution and having entries in a second dimension corresponding to one of the plurality of distinct wavelengths. In addition, various of the embodiments may include aspects discussed above in connection embodiments for other sensor systems.

In a fourth set of embodiments, a method is provided for determining a liveness state of a sample. The sample is illuminated with light at a plurality of discrete wavelengths. Light scattered within tissue of the sample is received. Multispectral characteristics of the received light are derived at the plurality of discrete wavelengths. A liveness state of the tissue is determined from the derived multispectral characteristics to ensure that the derived characteristics of the sample are consistent with the characteristics anticipated from an authentic sample. Various of the embodiments may include aspects discussed above for other sets of embodiments.

In a fifth set of embodiments, a method is provided for determining a blood-alcohol level of an individual. Electromagnetic radiation emanating from tissue of the individual in response to propagation of electromagnetic radiation into the tissue of the individual is received. Spectral properties of the received electromagnetic radiation are analyzed. The blood-alcohol level is determined from the analyzed spectral properties.

The spectral properties may be analyzed over specific wavelength ranges in specific embodiments. For example, in one embodiment amplitudes of the received electromagnetic radiation are determined within a wavelength range of 2.1-2.5 µm. This range includes the specific wavelengths of 2.23 µm, 2.26 µm, 2.28 µm, 2.30 µm, 2.32 µm, 2.25 µm, and 2.38 µm, at one or more of which amplitudes may be determined in a specific embodiment. In another embodiment, amplitudes of the received electromagnetic radiation are determined within a wavelength range of 1.5-1.9 µm. This range includes 1.67 µm, 1.69 µm, 1.71 µm, 1.73 µm, 1.74 µm 1.76 µm and 1.78 µm, at one or more of which amplitudes may be determined in a specific embodiment.

In a sixth set of embodiments, an apparatus is provided for determining a blood-alcohol level of an individual. A receiver is adapted to receive electromagnetic radiation emanating from tissue of the individual in response to propagation of electromagnetic radiation into the tissue of the individual. A computer readable-storage medium is coupled with a process and has a computer-readable program embodied therein for directing operation of the processor. The computer-readable program includes instructions for analyzing spectral properties of the received electromagnetic radiation and instructions for determining the blood-alcohol level from the analyzed spectral properties.

In some embodiments, the methods and/or apparatus of the invention may be embodied in devices, such as motor vehicles, whose access and/or operation may be dependent on the determination of the blood-alcohol level. Furthermore, the use of alcohol monitoring may be coupled with biometric identifications in some embodiments. For example, access and/or operation of devices embodying combined alcohol-monitoring and biometric-identification devices may be dependent on a combination of alcohol-monitoring and biometric-identification determinations. In one embodiment, the biometric identification is performed with the same multispectral data used to perform the alcohol estimation.

BRIEF DESCRIPTION OF THE DRAWINGS

A further understanding of the nature and advantages of the present invention may be realized by reference to the remaining portions of the specification and the drawings wherein like reference labels are used throughout the several drawings to refer to similar components. In some instances, reference labels include a numerical portion followed by a latin-letter suffix; reference to only the numerical portion of reference labels is intended to refer collectively to all reference labels that have that numerical portion but different latin-letter suffices.

DETAILED DESCRIPTION OF THE INVENTION

1. Overview

Figure 1:
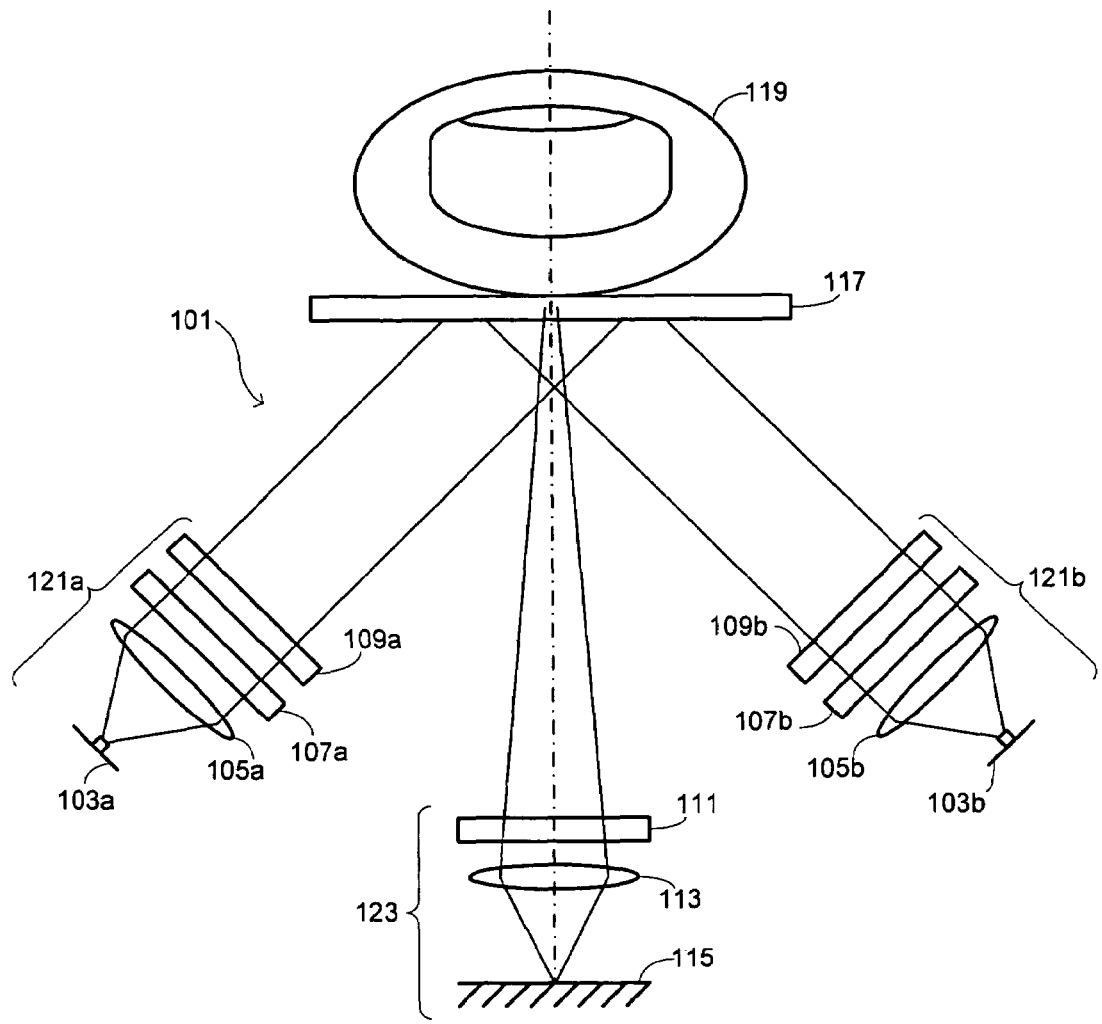
FIG. 1 provides a front view of a multispectral biometric sensor in one embodiment of the invention.

Embodiments of the invention provide methods and systems that allow for the collection and processing of integrated, multifactor biometric measurements. These integrated, multifactor biometric measurements may provide strong assurance of a person's identity, as well as of the authenticity of the biometric sample being taken. In some embodiments, a sensor provides a plurality of discrete optical wavelengths that penetrate the surface of the skin, and scatter within the skin and/or underlying tissue. As used herein, reference to "discrete wavelengths" is intended to refer to sets of wavelengths or wavelength bands that are treated as single binned units—for each binned unit, information is extracted only from the binned unit as a whole, and not from individual wavelength subsets of the binned unit. In some cases, the binned units may be discontinuous so that when a plurality of discrete wavelengths are provided, some wavelength between any pair of the wavelengths or wavelength bands is not provided, but this is not required in all embodiments. In one embodiment, the optical wavelengths are within the ultraviolet—visible—near-infrared wavelength range. A portion of the light scattered by the skin and/or underlying tissue exits the skin and is used to form a multispectral image of the structure of the tissue at and below the surface of the skin. As used herein, the term "multispectral" is intended to be construed broadly as referring to methods and systems that use multiple wavelengths, and thus includes imaging systems that are "hyperspectral" or "ultraspectral" as those terms are understood by those of skill in the art. Because of the wavelength-dependent properties of the skin, the image formed from each wavelength of light is usually different from images formed at other wavelengths. Accordingly, embodiments of the invention collect images from each of the wavelengths of light in such a way that characteristic spectral and spatial information may be extracted by an algorithm applied to the resulting multispectral image data.

In some applications, it may be desirable to estimate other parameters and characteristics of a body, either independently or in combination with a biometric measurement. For example, in one specific such embodiment, an ability is provided to measure blood-alcohol levels of a person simultaneously with measurement of a fingerprint pattern; such an embodiment has applications to law enforcement as well as to a variety of commercial applications including restricting motor-vehicle access. In this way, the analyte measurement and the identity of the person on whom the measurement is made may be inextricably linked.

Skin composition and structure is very distinct, very complex, and varies from person to person. By performing optical measurements of the spatio-spectral properties of skin and underlying tissue, a number of assessments may be made. For example, a biometric-identification function may be performed to identify or verify whose skin is being measured, a liveness function may be performed to assure that the sample being measured is live and viable skin and not another type of material, estimates may be made of a variety of physiological parameters such as age gender, ethnicity, and other demographic and anthropometric characteristics, and/or measurements may be made of the concentrations of various analytes and parameters including alcohol, glucose, degrees of blood perfusion and oxygenation, bilirubin, cholesterol, urea, and the like.

The complex structure of skin may be used in different embodiments to tailor aspects of the methods and systems for particular functions. The outermost layer of skin, the epidermis, is supported by the underlying dermis and hypodermis. The epidermis itself may have five identified sublayers that include the stratum corneum, the stratum lucidum, the stratum granulosum, the stratum spinosum, and the stratum germinativum. Thus, for example, the skin below the top-most stratum corneum has some characteristics that relate to the surface topography, as well as some characteristics that change with depth into the skin. While the blood supply to skin exists in the dermal layer, the dermis has protrusions into the epidermis known as "dermal papillae," which bring the blood supply close to the surface via capillaries. In the volar surfaces of the fingers, this capillary structure follows the structure of the friction ridges on the surface. In other locations on the body, the structure of the capillary bed may be less ordered, but is still characteristic of the particular location and person. As well, the topography of the interface between the different layers of skin is quite complex and characteristic of the skin location and the person. While these sources of subsurface structure of skin and underlying tissue represent a significant noise source for non-imaging optical measurements of skin for biometric determinations or analyte measurements, the structural differences are manifested by spectral features compared through embodiments of the invention.

In some instances, inks, dyes and/or other pigmentation may be present in portions of the skin as topical coating or subsurface tattoos. These forms of artificial pigmentation may or may not be visible to the naked human eye. However, if one or more wavelengths used by the apparatus of the present invention is sensitive to the pigment, the sensor can be used in some embodiments to verify the presence, quantity and/or shape of the pigment in addition to other desired measurement tasks.

In general, embodiments of the present invention relate to methods and systems for collecting spatio-spectral information in the form of multispectral images or datacubes. In certain instances, the desired information is contained in just a portion of the entire multispectral datacube. For example, estimation of a uniformly distributed, spectrally active compound may require just the measure spectral characteristics, which can be extracted from the overall multispectral datacube. In such cases, the overall system design may be simplified to reduce or eliminate the spatial component of the collected data by reducing the number of image pixels, even to a limit of a single pixel. Thus, while the systems and methods disclosed are generally described in the context of multispectral imaging, it will be recognized that the invention encompasses similar measurements in which the degree of imaging is greatly reduced, even to the point where there is a single detector element.

2. Exemplary Embodiments

One embodiment of the invention is depicted with the schematic diagram of FIG. 1, which shows a front view of a multispectral biometric sensor 101. The multispectral sensor 101 comprises an illumination subsystem 121 having one or more light sources 103 and a detection subsystem 123 with an imager 115. The figure depicts an embodiment in which the illumination subsystem 121 comprises a plurality of illumination subsystems 121a and 121b, but the invention is not limited by the number of illumination or detection subsystems 121 or 123. For example, the number of illumination subsystems 121 may conveniently be selected to achieve certain levels of illumination, to meet packaging requirements, and to meet other structural constraints of the multispectral biometric sensor 101. Illumination light passes from the source 103 through illumination optics 105 that shape the illumination to a desired form, such as in the form of flood light, light lines, light points, and the like. The illumination optics 105 are shown for convenience as consisting of a lens but may more generally include any combination of one or more lenses, one or more mirrors, and/or other optical elements. The illumination optics 105 may also comprise a scanner mechanism (not shown) to scan the illumination light in a specified one-dimensional or two-dimensional pattern. The light source 103 may comprise a point source, a line source, an area source, or may comprise a series of such sources in different embodiments. In one embodiment, the illumination light is provided as polarized light, such as by disposing a linear polarizer 107 through which the light passes before striking a finger 119 or other skin site of the person being studied.

In some instances, the light source 103 may comprise one or more quasimonochromatic sources in which the light is provided over a narrow wavelength band. Such quasimonochromatic sources may include such devices as light-emitting diodes, laser diodes, or quantum-dot lasers. Alternatively, the light source 103 may comprise a broadband source such as in incandescent bulb or glow bar. In the case of a broadband source, the illumination light may pass through a bandpass filter 109 to narrow the spectral width of the illumination light. In one embodiment, the bandpass filter 109 comprises one or more discrete optical bandpass filters. In another embodiment, the bandpass filter 109 comprises a continuously variable filter that moves rotationally or linearly (or with a combination of rotational and linear movement) to change the wavelength of illumination light. In still another embodiment, the bandpass filter 109 comprises a tunable filter element such as a liquid-crystal tunable filter, an acousto-optical tunable filter, a tunable Fabry-Perot filter or other filter mechanism known to one knowledgeable in the art.

After the light from the light source 103 passes through the illumination optics 105, and optionally the optical filter 109 and/or polarizer 107, it passes through a platen 117 and illuminates the finger 119 or other skin site. The sensor layout and components may advantageously be selected to minimize the direct reflection of the illumination into the detection optics 113. In one embodiment, such direct reflections are reduced by relatively orienting the illumination subsystem 121 and detection subsystem 123 such that the amount of directly reflected light detected is minimized. For instance, optical axes of the illumination subsystem 121 and the detection subsystem 123 may be placed at angles such that a mirror placed on the platen 117 does not direct an appreciable amount of illumination light into the detection subsystem 123. In addition, the optical axes of the illumination and detection subsystems 121 and 123 may be placed at angles relative to the platen 117 such that the angular acceptance of both subsystems is less than the critical angle of the system; such a configuration avoids appreciable effects due to total internal reflectance between the platen 117 and the skin site 119.

An alternative mechanism for reducing the directly reflected light makes use of optical polarizers. Both linear and circular polarizers can be employed advantageously to make the optical measurement more sensitive to certain skin depths, as known to one familiar in the art. In the embodiment illustrated in FIG. 1, the illumination light is polarized by linear polarizer 107. The detection subsystem 123 may then also include a linear polarizer 111 that is arranged with its optical axis substantially orthogonal to the illumination polarizer 107. In this way, light from the sample must undergo multiple scattering events to significantly change its state of polarization. Such events occur when the light penetrates the surface of the skin and is scattered back to the detection subsystem 123 after many scatter events. In this way, surface reflections at the interface between the platen 117 and the skin site 119 are reduced.

The detection subsystem 123 may incorporate detection optics that comprise lenses, mirrors, and/or other optical elements that form an image of the region near the platen surface 117 onto the detector 115. The detection optics 113 may also comprise a scanning mechanism (not shown) to relay portions of the platen region onto the detector 115 in sequence. In all cases, the detection subsystem 123 is configured to be sensitive to light that has penetrated the surface of the skin and undergone optical scattering within the skin and/or underlying tissue before exiting the skin.

The illumination subsystem 121 and detection subsystem 123 may be configured to operate in a variety of optical regimes and at a variety of wavelengths. One embodiment uses light sources 103 that emit light substantially in the region of 400-1000 nm; in this case, the detector 115 may be based on silicon detector elements or other detector material known to those of skill in the art as sensitive to light at such wavelengths. In another embodiment, the light sources 103 may emit radiation at wavelengths that include the near-infrared regime of 1.0-2.5 µm, in which case the detector 115 may comprise elements made from InGaAs, InSb, PbS, MCT, and other materials known to those of skill in the art as sensitive to light at such wavelengths.

Figure 2A:
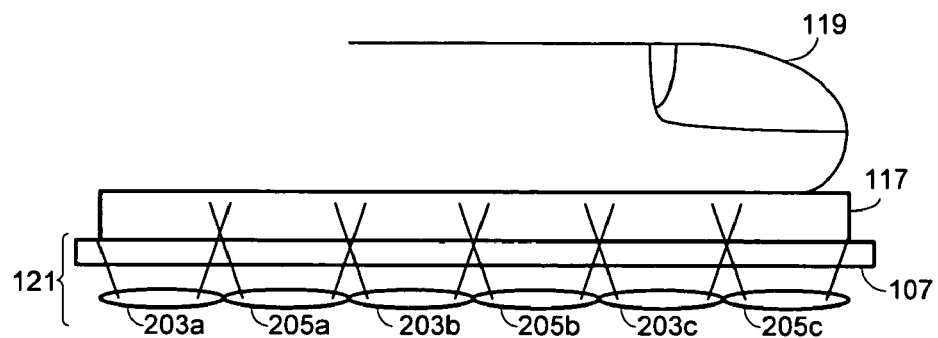
FIG. 2A provides a side view of a multispectral biometric sensor shown in one embodiment.

A side view of one of the embodiments of the invention is shown with the schematic drawing provided in FIG. 2A. For clarity, this view does not show the detection subsystem, but does show an illumination subsystem 121 explicitly. The illumination subsystem 121 in this embodiment includes two discrete light sources 203 and 205 that have different wavelength characteristics. For example, the light sources 203 and 205 may be quasimonochromatic sources such as LEDs, which do not require an optical filter. Sources 203a, 203b, and 203c may provide illumination with substantially the same first wavelength while sources 205a, 205b, and 205c may provide illumination with substantially the same second wavelength, different from the first wavelength. As shown, the illumination optics in FIG. 2A are configured to provide flood illumination, but in alternative embodiments could be arranged to provide line, point, or other patterned illumination by incorporation of cylindrical optics, focusing optics, or other optical components as known to those knowledgeable in the art.

An exemplary measurement sequence for the system shown in FIG. 2A comprising activating the first light sources 203 and collecting a resulting image. After the image is acquired, the first light sources 203 are turned off and the second light sources 205 are activated at a different wavelength, and a resulting image is collected. For a sensor having more than one wavelength of light source, this illumination-measurement sequence is repeated for all the different wavelengths used in the sensor. It will also be appreciated that substantially the same sequence may be used in embodiments in which the wavelength characteristics of light are determined by states of tunable optical filters, variable optical filters, moveable discrete optical filters, and the like. Also, an alternative mechanism for collecting images at multiple wavelengths may incorporate an encoding method to identify light of each wavelength when multiple wavelengths are illuminated at a given time. The data from the entire illumination sequence is then collected in such a way that the individual wavelength responses are determined from the encoding using methods known to those of skill in the art. Illumination techniques thus include round-robin, frequency-division modulation, Hadamard encoding, and others.

The sequence of illumination of the light sources may be changed from measurement to measurement. This variability may be introduced to thwart replay attacks where a set of valid signals is recorded and replayed at a later time to defeat the biometric sensor. The measurement variability from sample to sample may also extend in some embodiments to using only a subset of available illumination wavelengths, which are then compared with the corresponding subset of data in an enrollment dataset.

The array of light sources 203 and 205 need not actually be planar as shown in FIG. 2A. For example, in other embodiments, optical fibers, fiber bundles, or fiber optical faceplates or tapers could convey the light from the light sources at some convenient locations to an illumination plane, where light is reimaged onto the finger. The light sources could be controlled by turning the drive currents on and off as LEDs might be. Alternatively, if an incandescent source is used, rapid switching of the light may be accomplished using some form of spatial light modulator such as a liquid crystal modulator or using microelectromechanical-systems ("MEMS") technology to control apertures, mirrors, or other such optical elements.

Figure 2B:
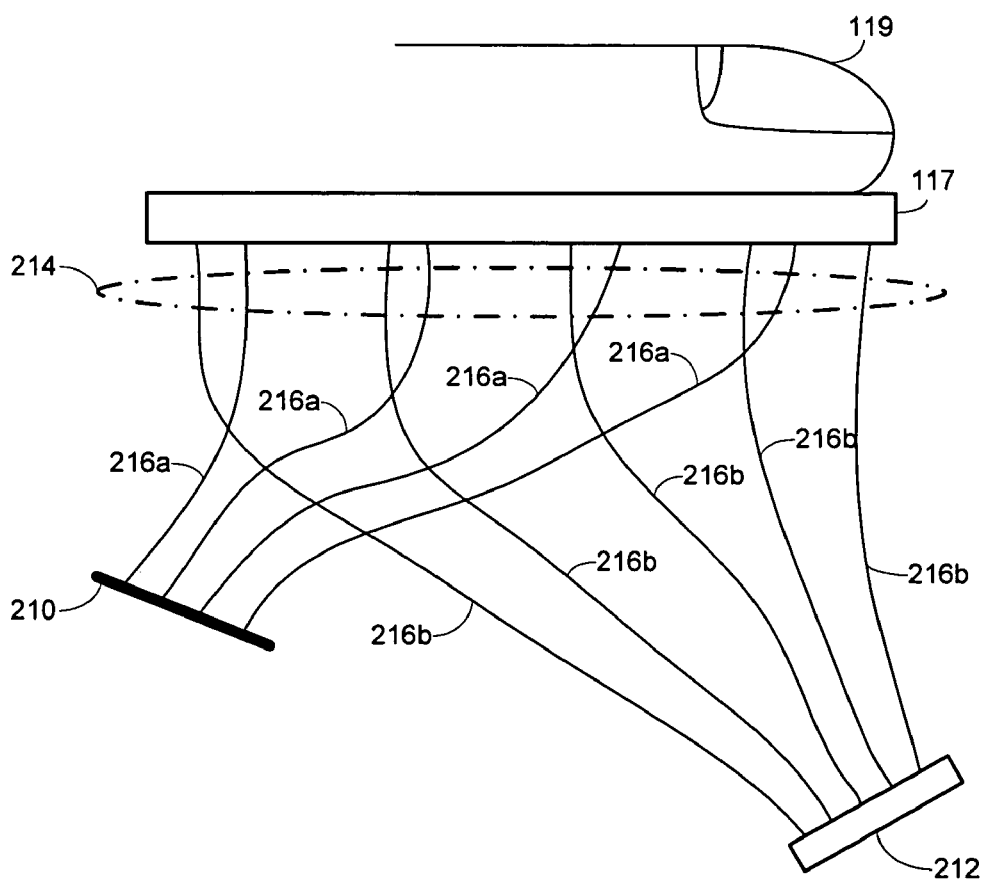
FIG. 2B provides a side view of a multispectral biometric sensor shown in another embodiment.

The use of optical components such as optical fibers and fiber bundles may allow the structure of the multispectral biometric sensor to be simplified. One embodiment is illustrated in FIG. 2B, which shows the use of optical fibers and electronic scanning of illumination sources such as LEDs. Individual fibers 216a connect each of the LEDs located at an illumination array 210 to an imaging surface, and other fibers 216b relay the reflected light back to the imaging device 212, which may comprise a photodiode array or CCD array. The set of fibers 216a and 216b thus defines an optical fiber bundle 214 used in relaying light.

Figure 3:
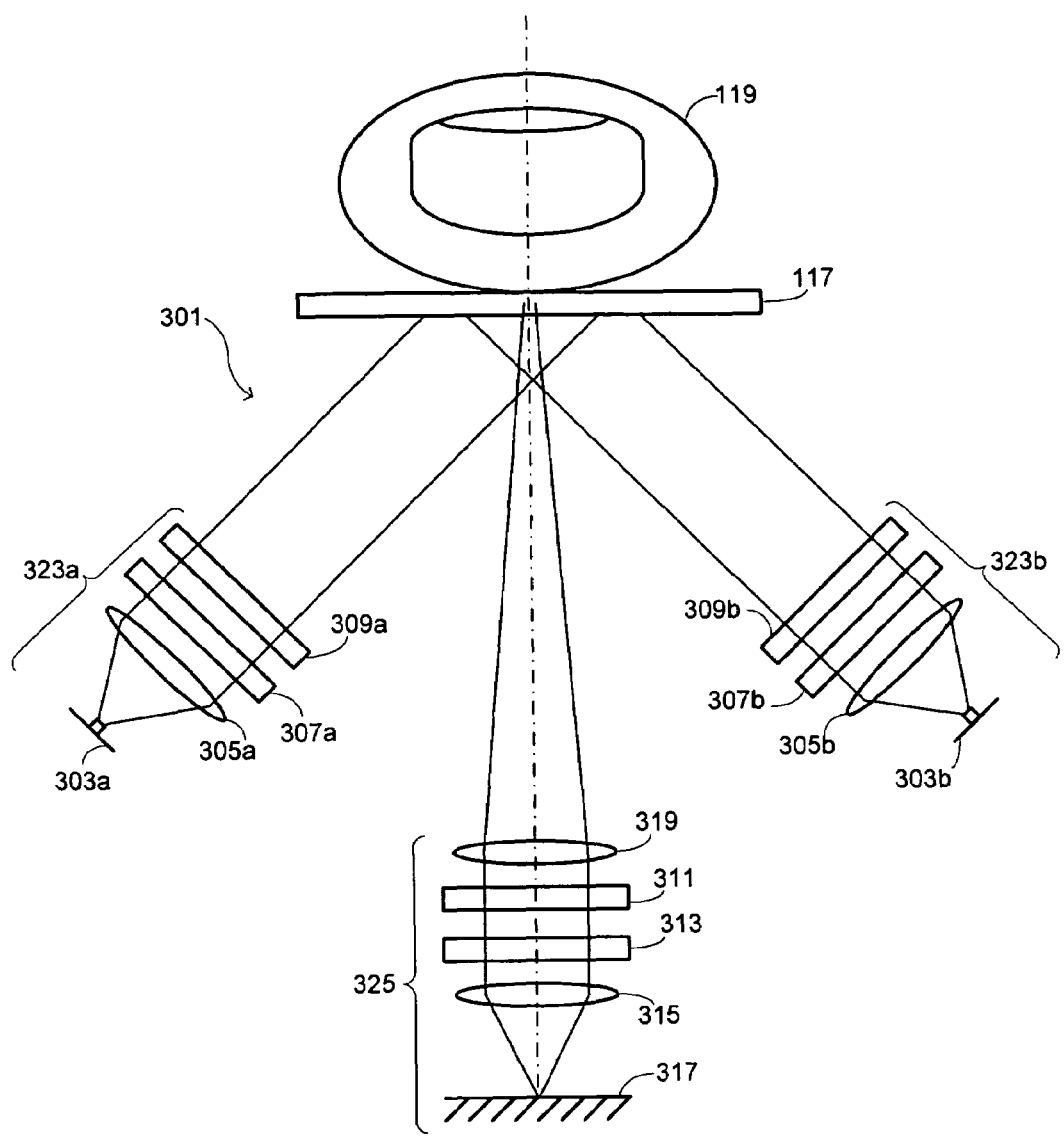
FIG. 3 provides a front view of a computer tomographic imaging spectrometer ("CTIS") in one embodiment of the invention.

Another embodiment of the invention is shown schematically with the front view of FIG. 3. In this embodiment, the multispectral biometric sensor 301 comprises a broadband illumination subsystem 323 and a detection subsystem 325. As for the embodiment described in connection with FIG. 1, there may be multiple illumination subsystems 323 in some embodiments, with FIG. 3 showing a specific embodiment having two illumination subsystems 323. A light source 303 comprised by the illumination subsystem 323 is a broadband illumination source such as an incandescent bulb or a glowbar, or may be any other broadband illumination source known to those of skill in the art. Light from the light source 303 passes through illumination optics 305 and a linear polarizer 307, and may optionally pass through a bandpass filter 309 used to limit the wavelengths of light over a certain region. The light passes through a platen 117 and into a skin site 119. A portion of the light is diffusely reflected from the skin 119 into the detection subsystem 325, which comprises imaging optics 315 and 319, a crossed linear polarizer 311, and a dispersive optical element 313. The dispersive element 313 may comprise a one- or two-dimensional grating, which may be transmissive or reflective, a prism, or any other optical component known in the art to cause a deviation of the path of light as a function of the light's wavelength. In the illustrated embodiment, the first imaging optics 319 acts to collimate light reflected from the skin 119 for transmission through the crossed linear polarizer 311 and dispersive element 313. Spectral components of the light are angularly separated by the dispersive element 313 and are separately focused by the second imaging optics 315 onto a detector 317. As discussed in connection with FIG. 1, the polarizers 307 and 311 respectively comprised by the illumination and detection subsystems 323 and 325 act to reduce the detection of directly reflected light at the detector 317.

The multispectral image generated from light received at the detector is thus a "coded" image in the manner of a computer tomographic imaging spectrometer ("CTIS"). Both wavelength and spatial information are simultaneously present in the resulting image. The individual spectral patterns may be obtained by mathematical inversion or "reconstruction" of the coded image.

Figure 4:
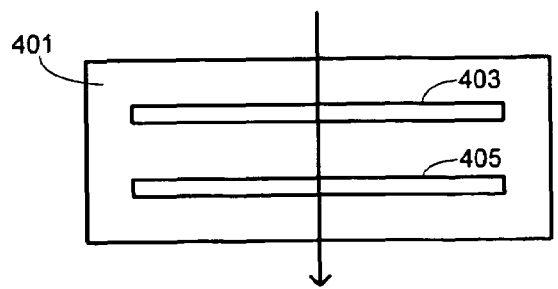
FIG. 4 provides a top view of a swipe sensor in an embodiment of the invention.

The embodiments described above in connection with FIGS. 1-3 are examples of "area" sensor configurations. In addition to such area sensor configurations, multispectral imaging sensors may be configured as "swipe" sensors in some embodiments. One example of a swipe sensor is shown in top view with the schematic illustration of FIG. 4. In this figure, the illumination region 403 and detection region 405 of a sensor 401 are substantially collinear. In some embodiments of a swipe sensor 401, there may be more than a single illumination region. For example, there may be a plurality of illumination regions arranged on either side of the detection region 405. In some embodiments, the illumination region 403 may partially or fully overlap the detection region 405. The multispectral image data are collected with the sensor 401 by swiping a finger or other body part across the optically active region, as indicated by the arrow in FIG. 4. The corresponding linear sensor may be a stationary system or a roller system that may further include an encoder to record the position information and aid in stitching a full two-dimensional image from a resulting series of image slices as known to one knowledgeable in the art. When the roller system is used, a fingertip or other skin site may be rolled over a roller that is transparent to the wavelengths of light used. The light is then sequentially received from discrete portions of the skin site, with the multispectral image being built up from light received from the different portions.

The polarizers included with some embodiments may also be used to create or further accentuate the surface features. For instance, if the illumination light is polarized in a direction parallel ("P") with the sampling platen and the detection subsystem incorporates a polarizer in a perpendicular orientation ("S"), then the reflected light is blocked by as much as the extinction ratio of the polarizer pair. However, light that crosses into the fingertip at a ridge point is optically scattered, which effectively randomizes the polarization. This allows a portion, on the order of 50%, of the absorbed and re-emitted light to be observed by the S-polarized imaging system.

The systems described in connection with the specific embodiments above are illustrative and are not intended to be limiting. There are numerous variations and alternatives to the exemplary embodiments described above that are also within the intended scope of the invention. In many instances, the layout or order of the optical components may be changed without substantially affecting functional aspects of the invention. For example, in embodiments that use broadband illumination sources and one or more optical filters, the filter(s) may be located at any of a variety of points in both the illumination and detection subsystems. Also, while the figures show the finger or other skin site from which measurements are made being in contact with the platen, it will be evident that substantially the same measurements may be made without such contact. In such instances, the optical systems for illumination and detection may be configured to illuminate and image the skin site at a distance. Some examples of such systems are provided in U.S. Prov. Pat. Appl. No. 60/552,662, entitled "OPTICAL SKIN SENSOR FOR BIOMETRICS," filed Mar. 10, 2004, which has been incorporated by reference.

Figure 5:
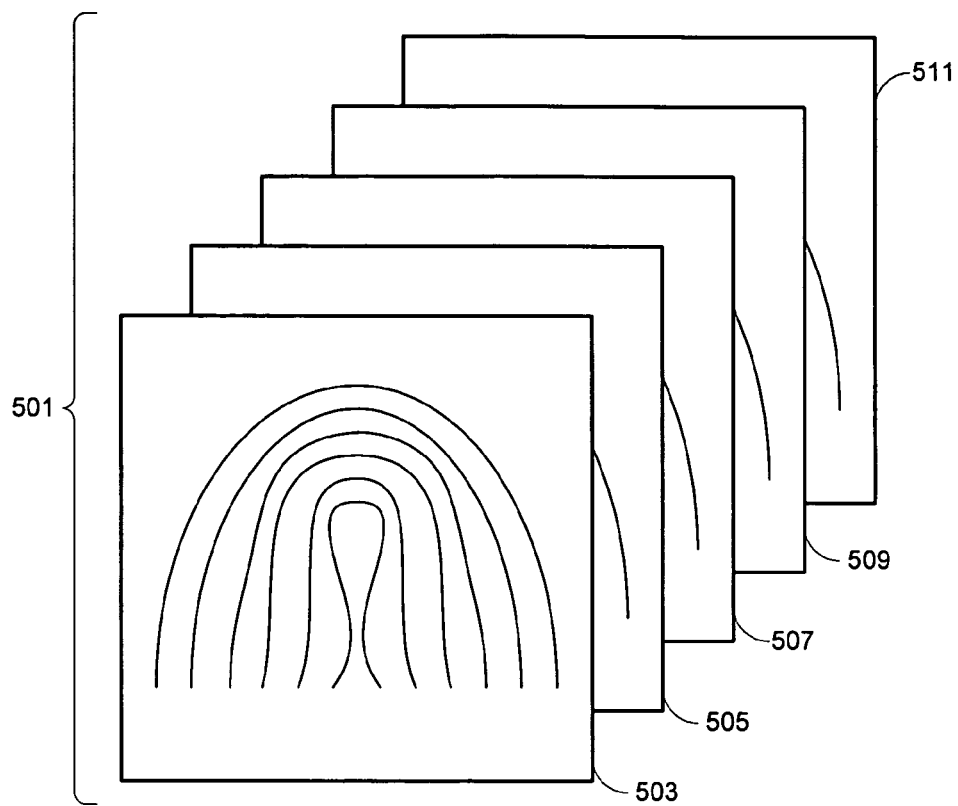
FIG. 5 illustrates a multispectral datacube generated in accordance with embodiments of the invention.

The embodiments described above produce a set of images of the skin site at different wavelengths or produce data from which such a set may be produced using reconstruction techniques, such as in the particular case of the CTIS or encoded illumination subsystems. For purposes of illustration, the following discussion is made with reference to such a set of spectral images, although it in not necessary to produce them for subsequent biometric processing in those embodiments that do not generate them directly. An illustrative set of multispectral images is shown in FIG. 5, with the set defining a multispectral datacube 501.

One way to decompose the datacube 501 is into images that correspond to each of the wavelengths used in illuminating the sample in the measurement process. In the figure, five separate images 503, 505, 507, 509, and 511 are shown, corresponding to five discrete illumination wavelengths and/or illumination conditions (e.g. illumination point source at position X, Y). In an embodiment where visible light is used, the images might correspond, for example, to images generated using light at 450 nm, 500 nm, 550 nm, 600 nm, and 650 nm. Each image represents the optical effects of light of a particular wavelength interacting with skin and, in the case of embodiments where the skin is in contact with a platen during measurement, represents the combined optical effects of light of a particular wavelength interacting with skin and also passing through the skin-platen interface. Due to the optical properties of skin and skin components that vary by wavelength, each of the multispectral images 503, 505, 507, 509, and 511 will be, in general, different from the others The datacube may thus be expressed as $R(X_S, Y_S, X_I, Y_I, \lambda)$ and describes the amount of diffusely reflected light of wavelength $\mu$ seen at each image point $X_I, Y_I$ when illuminated at a source point $X_S, Y_S$. Different illumination configurations (flood, line, etc.) can be summarized by summing the point response over appropriate source point locations. A conventional non-TIR fingerprint image $F(X_I, Y_I)$ can loosely be described as the multispectral data cube for a given wavelength, $\lambda_0$, and summed over all source positions:

$$F(X_I, Y_I) = \sum_{Y_S}\sum_{X_S} R(X_S, Y_S, X_I, Y_I, \lambda_0).$$

Conversely, the spectral biometric dataset $S(\lambda)$ relates the measured light intensity for a given wavelength $\lambda$ to the difference $\vec{D}$ between the illumination and detection locations:

$$S(\vec{D}, \lambda) = R(X_I - X_S, Y_I - Y_S, \lambda).$$

The multispectral datacube R is thus related to both conventional fingerprint images and to spectral biometric datasets. The multispectral datacube R is a superset of either of the other two data sets and contains correlations and other information that may be lost in either of the two separate modalities.

The optical interactions at the skin-platen interface will be substantially the same at all wavelengths since the optical qualities of the platen material and the skin are not generally significantly different over the range of wavelengths used and the optical interface does not change substantially during the measurement interval. Light migrated from the skin to the platen, as well as from the platen to the skin, will be affected by Fresnel reflections at the optical interfaces. Thus, light that traverses an air gap will be less intense in the receiving medium than light that does not cross an air gap. This phenomenon forms just one portion of the image information that is contained in the multispectral datacube.

Figure 6:
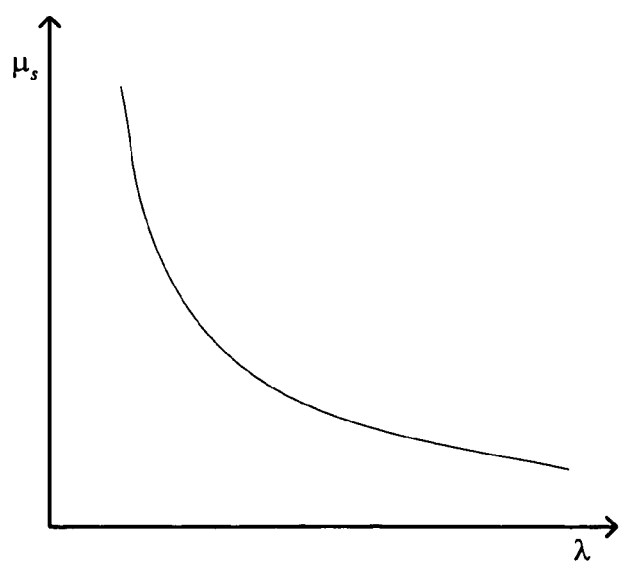
FIG. 6 is a graphical illustration of the effects of skin scatter.
Figure 7:
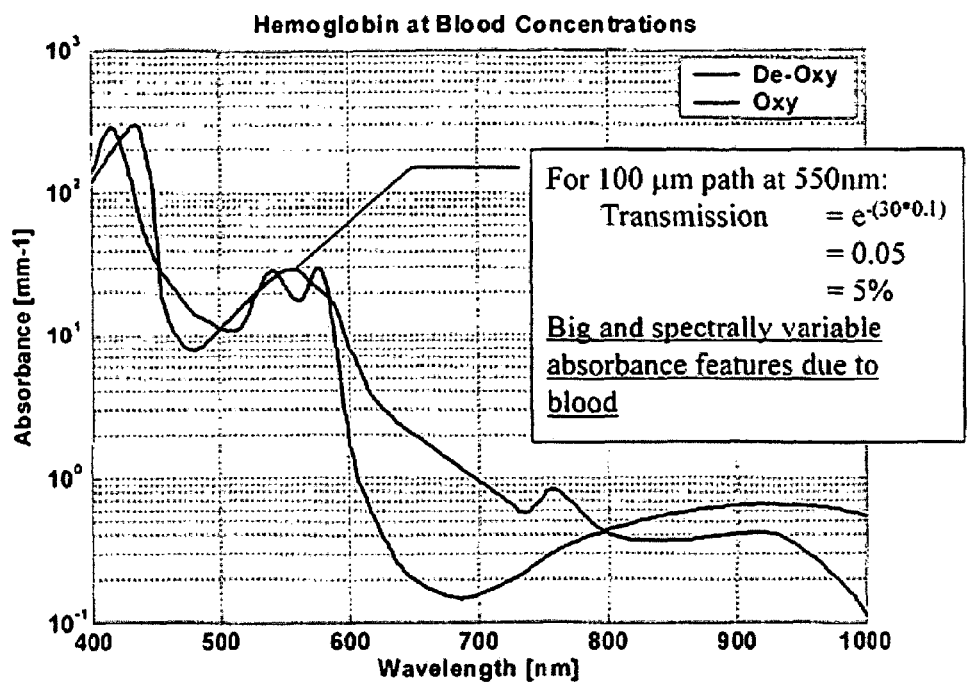
FIG. 7 provides a graphical illustration of the effects of blood absorbance.

The light that passes into the skin and/or underlying tissue is generally affected by different optical properties of the skin and/or underlying tissue at different wavelengths. Two optical effects in the skin and/or underlying tissue that are affected differently at different wavelengths are scatter and absorbance. Optical scatter in skin tissue is generally a smooth and relatively slowly varying function of wavelength, as shown in FIG. 6. Conversely, absorbance in skin is generally a strong function of wavelength due to particular absorbance features of certain components present in the skin. For example, blood has certain characteristic absorbance features as shown in FIG. 7. In addition to blood, other substances that have significant absorbance properties in the spectral region from 400 nm to 2.5 µm and that are found in skin and/or underlying tissue include melanin, water, carotene, biliruben, ethanol, and glucose.

Figure 8:
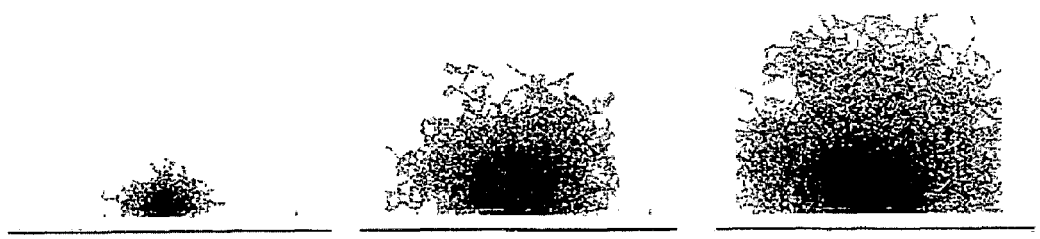
FIG. 8 provides examples of different illumination characteristics that may be used in embodiments of the invention.

The combined effect of optical absorbance and scatter causes different illumination wavelengths to penetrate the skin to different depths. This effect is illustrated schematically in FIG. 8, which depicts the optical scattering that occurs in tissue for three different illumination points on the surface of skin at three different wavelengths, shown with the same scale. This phenomenon effectively causes the different spectral images to have different and complementary information corresponding to different volumes of the illuminated tissue. In particular, the capillary layers close to the surface of the skin have distinct spatial characteristics that can be imaged using wavelengths of light in which blood is strongly absorbing.

Thus, the multispectral image datacube contains spatio-spectral information from multiple sources. Merely by way of example, for the case of a measurement taken on the fingertip in contact with a platen, the resulting datacube contains effects due to: (i) the optical interface between the fingertip and the platen, similar to information contained in a conventional non-TIR fingerprint; (ii) the overall spectral characteristics of the tissue, which are distinct from person to person; (iii) the blood vessels close to the surface of the skin, similar to vein imaging; and (iv) the blood vessels and other spectrally active structures distributed deeper in the tissue. As such, embodiments of the invention provide a mechanism for extracting biometric data from multiple sources within the fingertip or other skin site being measured, thereby providing multifactor biometric-sensing applications.

Because of the complex wavelength-dependent properties of skin and underlying tissue, the set of spectral values corresponding to a given image location has spectral characteristics that are well-defined and distinct. These spectral characteristics may be used to classify the multispectral image data on a pixel-by-pixel basis. This assessment may be performed by generating typical tissue spectral qualities from a set of qualified images. For example, the multispectral data shown in FIG. 5 may be reordered as an N×5 matrix, where N is the number of image pixels that contain data from living tissue, rather than from a surrounding region of air. An eigenanalysis or other factor analysis performed on this set matrix produces the representative spectral features of these tissue pixels. The spectra of pixels in a later data set may then be compared to such previously established spectral features using metrics such as Mahalanobis distance and spectral residuals. If more than a small number of image pixels have spectral qualities that are inconsistent with living tissue, then the sample is deemed to be non-genuine and rejected, thus providing a mechanism for incorporating antispoofing methods in the sensor based on determinations of the liveness of the sample.

Similarly, in an embodiment where the sample is a fingertip, the multispectral image pixels are classified as "ridge," "valley," or "other," based on their spectral qualities. This classification can be performed using discriminant analysis methods such as linear discriminant analysis, quadratic discriminant analysis, principle component analysis, neural networks, and others known to those of skill in the art. Since ridge and valley pixels are contiguous on a typical fingertip, in some instances multispectral data from the local neighborhood around the image pixel of interest are used to classify the image pixel. In this way, a conventional fingerprint image is extracted from the sensor for further processing and biometric assessment. The "other" category may indicate image pixels that have spectral qualities that are different than anticipated in a genuine sample. A threshold on the total number of pixels in an image classified as "other" may be set. If this threshold is exceeded, the sample may be determined to be non-genuine and appropriate indications made and actions taken.

Biometric determinations of identity may be made using the entire datacube or particular portions thereof. For example, appropriate spatial filters may be applied to separate out the lower spatial frequency information that is typically representative of deeper spectrally active structures in the tissue. The fingerprint data may be extracted using similar spatial frequency separation and/or the pixel classification methods disclosed above. The spectral information can be separated from the active portion of the image in the manner discussed above. These three portions of the datacube may then be processed and compared to the corresponding enrollment data using methods known to one familiar with the art to determine the degree of match. Based upon the strength of match of these characteristics, a decision can be made regarding the match of the sample with the enrolled data.

As previously noted, certain substances that may be present in the skin and underlying tissue have distinct absorbance characteristics. For example, ethanol has characteristic absorbance peaks at approximately 2.26 µm, 2.30 µm, and 2.35 µm, and spectral troughs at 2.23 µm, 2.28 µm, 2.32 µm, and 2.38 µm. In some embodiments, noninvasive optical measurements are performed at wavelengths in the range of 2.1-2.5 µm, more particularly in the range of 2.2-2.4 µm. In an embodiment that includes at least one of the peak wavelengths and one of the trough wavelengths, the resulting spectral data are analyzed using multivariate techniques such as partial least squares, principal-component regression, and others known to those of skill in the art, to provide an estimate of the concentration of alcohol in the tissue, as well as to provide a biometric signature of the person being tested. While a correlation to blood-alcohol level may be made with values determined for a subset of these wavelengths, it is preferable to test at least the three spectral peak values, with more accurate results being obtained when the seven spectral peak and trough values are measured.

In other embodiments, noninvasive optical measurements are performed at wavelengths in the range of 1.5-1.9 µm, more particularly in the range of 1.6-1.8 µm. In specific embodiments, optical measurements are performed at one or more wavelengths of approximately 1.67 µm, 1.69 µm, 1.71 µm, 1.73 µm, 1.74 µm 1.76 µm and 1.78 µm. The presence of alcohol is characterized at these wavelengths by spectral peaks at 1.69 µm, 1.73 µm, and 1.76 µm and by spectral troughs at 1.67 µm, 1.71 µm, 1.74 µm, and 1.78 µm. Similar to the 2.1-2.5 µm wavelength range, the concentration of alcohol is characterized by relative strengths of one or more of the spectral peak and trough values. Also, while a correlation to blood-alcohol level may be made with values determined for a subset of these wavelengths in the 1.5-1.9 µm range, it is preferable to test at least the three spectral peak values, with more accurate results being obtained when the seven spectral peak and trough values are measured.

A small spectral alcohol-monitoring device may be embedded in a variety of systems and applications in certain embodiments. The spectral alcohol-monitoring device can be configured as a dedicated system such as may be provided to law-enforcement personnel, or may be integrated as part of an electronic device such as an electronic fob, wristwatch, cellular telephone, PDA, or any other electronic device, for an individual's personal use. Such devices may include mechanisms for indicating to an individual whether his blood-alcohol level is within defined limits. For instance, the device may include red and green LEDs, with electronics in the device illuminating the green LED if the individual's blood-alcohol level is within defined limits and illuminating the red LED if it is not. In one embodiment, the alcohol-monitoring device may be included in a motor vehicle, typically positioned so that an individual may conveniently place tissue, such as a fingertip, on the device. While in some instances, the device may function only as an informational guide indicating acceptability to drive, in other instances ignition of the motor vehicle may affirmatively depend on there being a determination that the individual has a blood-alcohol level less than a prescribed level.

Figure 9A:
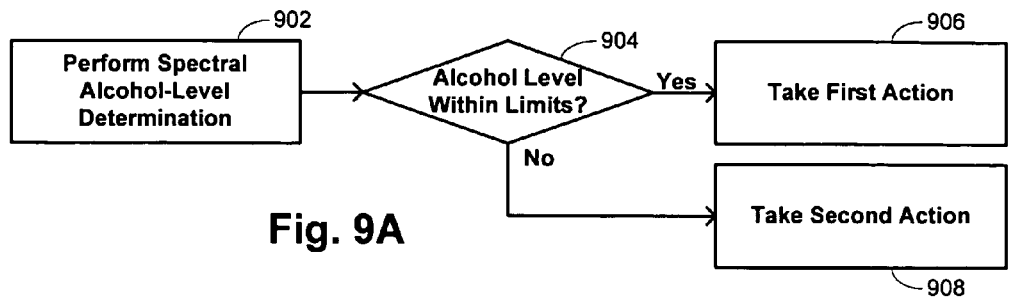
FIG. 9A provides a flow diagram illustrating a method for using an alcohol monitor in accordance with an embodiment of the invention.

This type of action is an example of a more general set of actions that may be performed with the alcohol-monitoring devices of the invention. Such general methods as they may be implemented by the alcohol-monitoring device are summarized in FIG. 9A. At block 902, an alcohol-level determination is performed with spectral information as described above. At block 904, a determination is made from the alcohol-level determination whether the alcohol level is within prescribed limits. If it conforms with such limits, a first action is taken at block 906. This action may correspond, for example, to allowing ignition of a motor vehicle, allowing a pilot to enter an aircraft, allowing an employee to enter a workplace, and the like. If the alcohol-level determination does not conform to the prescribed limits, a second action is taken at block 908. This action may correspond, for example, to preventing ignition of a motor vehicle, prohibiting access by a pilot to an aircraft or an employee to a workplace, and the like.

In some instances, the blood-alcohol determination may be coupled with a biometric determination. An overview of such combined methods is provided with the flow diagram of FIG. 9B. At block 910, an alcohol-level determination is performed using spectral information as described above. Different actions may be taken depending on whether the determined alcohol level is within prescribed limits, as tested at block 912. If the alcohol limit is outside the prescribed limits, a first action may be taken at block 914, such as prohibiting ignition of a motor vehicle. Access to the motor vehicle might, however, not automatically be granted by the system merely because the alcohol level was within the prescribed limits. As indicated at block 916, a determination that those limits are met may instead prompt a biometric test to be performed so that a check of an individual's identity is performed at block 918. If the person is identified as a specific person, such as the owner of the motor vehicle, a second action allowing access to the motor vehicle may be taken at block 920. If the person identified is not the specific person, a third action may be taken at block 922. This third action could correspond, for example, to the first action so that access to the motor vehicle is restricted, but could alternatively correspond to an action different from the first or second actions. For example, the third action could result in the sounding of an alarm to indicate that an unknown person is attempting to gain control of a motor vehicle.

Figure 9B:
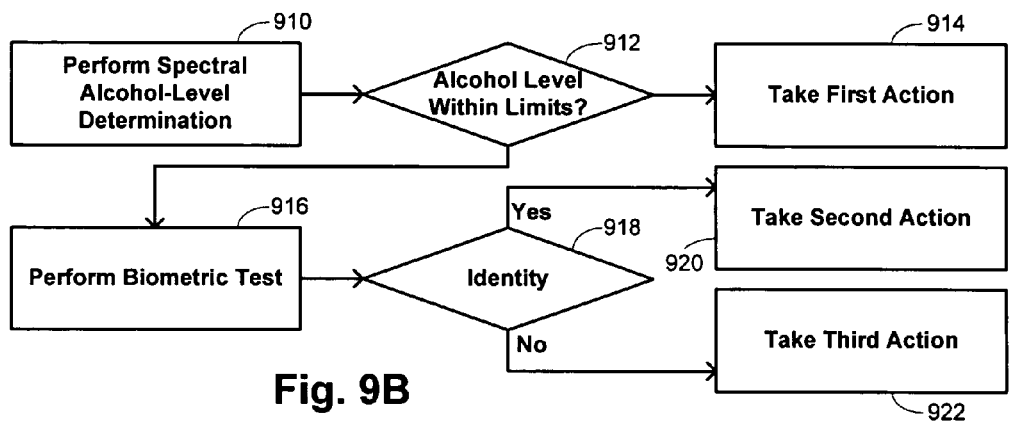
FIG. 9B provides a flow diagram illustrating a method for using a combination of an alcohol monitor and a biometric sensor with an embodiment of the invention.

The flow diagrams in FIG. 9B provide examples where a biometric test may be used to override a decision that would be made in response to a particular result of an alcohol-monitoring test. In other embodiments, a biometric test could be performed in response to the contrary result for the alcohol-monitoring test, or could be performed irrespective of the result of the alcohol-monitoring test. In such cases, different actions could be taken depending on the various combinations of results of the alcohol-level and biometric determinations. Furthermore, there is no need for the alcohol-monitoring test to precede the biometric determination; the tests could be performed in a different order or simultaneously in different embodiments.

Figure 9C:
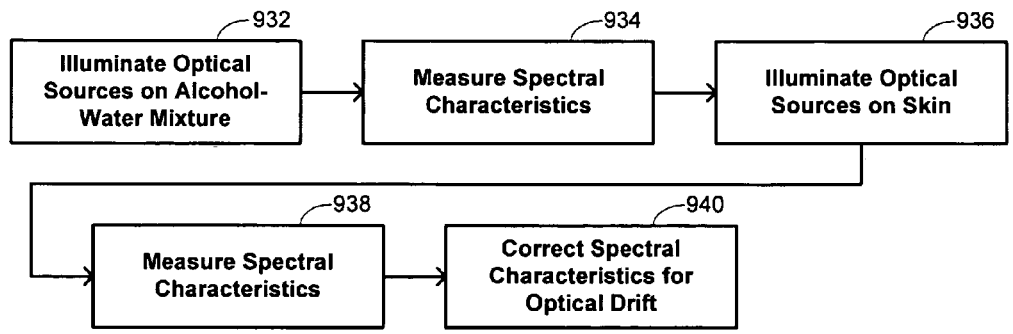
FIG. 9C provides a flow diagram illustrating a method for accommodating optical drift in embodiments of the invention.

In some embodiments, correction is made for optical drift by determining an optical correction from use of the alcohol-monitoring device on a reference sample. An overview of a method for making such a correction is provided in FIG. 9C. At block 932, optical sources of the alcohol-monitoring device are used to illuminate the reference sample, which could conveniently comprise an alcohol-water mixture. At block 934, a detector of the alcohol-monitoring device is used to measure spectral characteristics of light after propagation through the reference sample. These spectral characteristics are usually stored for later application to a variety of different spectral determinations. Thus, at block 936, the light sources of the alcohol-monitoring device are used to illuminate tissue of an individual and at block 938, the spectral characteristics of light propagated through the tissue are measured with a detector of the alcohol-monitoring device. Before making a determination of blood-alcohol level using the peak-trough comparison analysis described above, the spectral characteristics are corrected in accordance with the spectral characteristics determined from the reference sample at block 940. Changes that occur to the light sources, detectors, optical filters, lenses, mirrors, and other components in the optical chain will affect both the in vivo measurement and the reference sample in a similar manner. Processing of the in vivo sample in conjunction with the alcohol-bearing reference sample thus compensates for such optical effects.

Figure 10:
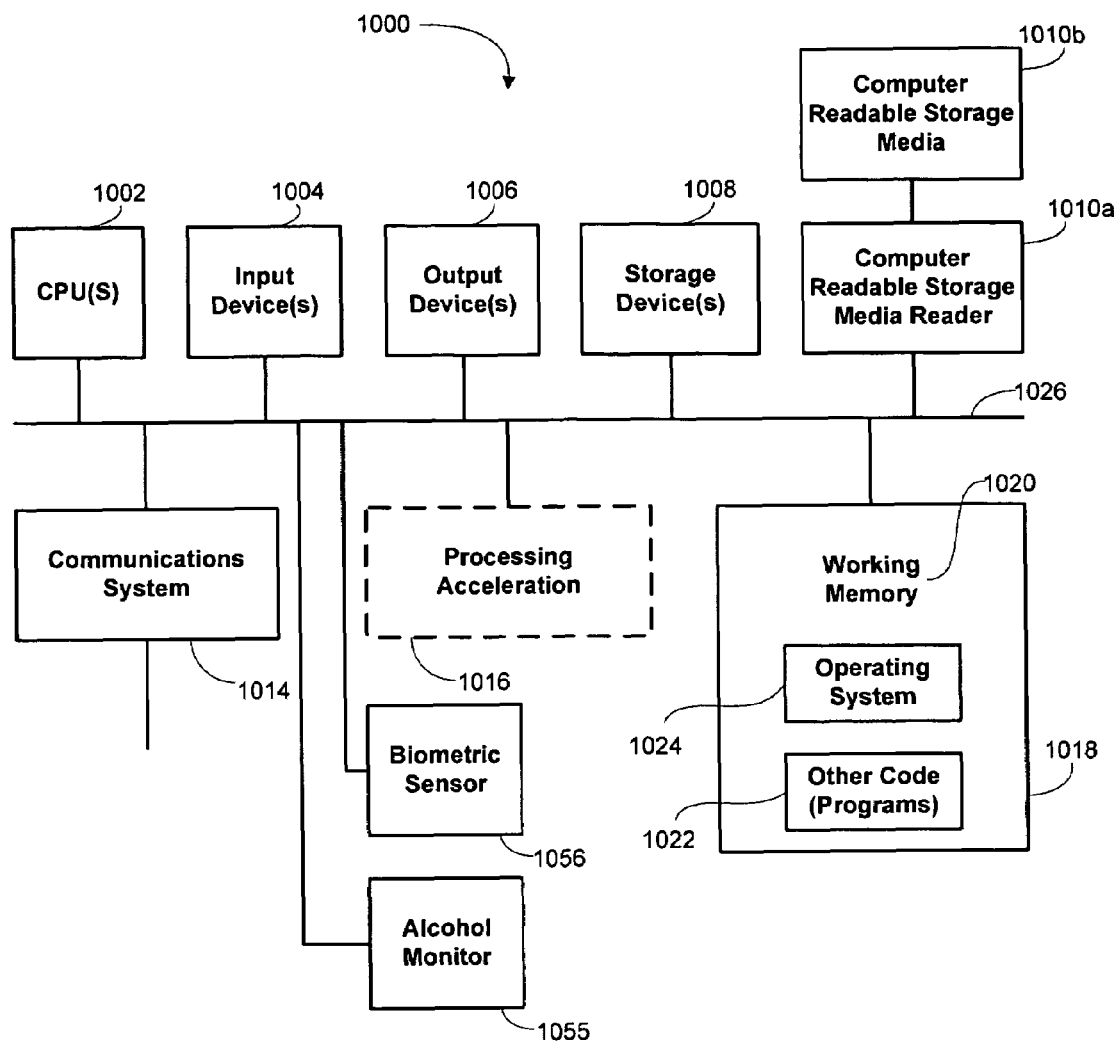
FIG. 10 provides a schematic representation of a computer system that may be used to manage functionality of alcohol monitors in accordance with embodiments of the invention.

Management of the functionality discussed herein for the alcohol-monitoring device may be performed with a computer system. The arrangement shown in FIG. 10 includes a number of components that may be appropriate for a larger system; smaller systems that are integrated with portable devices may use fewer of the components. FIG. 10 broadly illustrates how individual system elements may be implemented in a separated or more integrated manner. The computational device 1000 is shown comprised of hardware elements that are electrically coupled via bus 1026, which is also coupled with the alcohol-monitoring device 1055. The hardware elements include a processor 1002, an input device 1004, an output device 1006, a storage device 1008, a computer-readable storage media reader 1010a, a communications system 1014, a processing acceleration unit 1016 such as a DSP or special-purpose processor, and a memory 1018. The computer-readable storage media reader 1010a is further connected to a computer-readable storage medium 1010b, the combination comprehensively representing remote, local, fixed, and/or removable storage devices plus storage media for temporarily and/or more permanently containing computer-readable information. The communications system 1014 may comprise a wired, wireless, modem, and/or other type of interfacing connection and permits data to be exchanged with external devices.

The computational device 1000 also comprises software elements, shown as being currently located within working memory 1020, including an operating system 1024 and other code 1022, such as a program designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed FIG. 10 also indicates that a biometric sensor 1056 may also be coupled electrically via bus 1026 for use in those embodiments that combine the use of the alcohol-monitoring device 1055 with the biometric sensor 1056. As previously mentioned, the biometric sensor 1056 may also use spectral information in making identifications of individuals, although this is not required. The computational device 1000 may equally well be adapted to coordinate the function of any other type of biometric identification device with the alcohol-monitoring device as described above.

Other analytes in the body may be estimated using similar techniques by ensuring that the multispectral data that are measured by the sensor include characteristic absorbance features of the analyte of interest. Such analyte estimation techniques may be further aided using a method similar to the pixel classification technique described above. In such embodiments, the multispectral image pixels are classified as "ridge" or "valley," or are classified according to another appropriate classification such as "blood vessel" or "no vessel." A subset of the multispectral data is the extracted and used for the analyte estimation based on the pixel classification. This procedure reduces the variability of the estimation due to optical and physiological differences across the image plane.

Furthermore, the structural configurations for the sensors described herein may vary to reflect consideration of such facts as the cost and availability of off-the-shelf components, materials, designs, and other issues. Certain configurations may be easier, less expensive, and quicker to build than others, and there may be different considerations that affect prototype and volume productions differently. For all embodiments, the optical geometry should be carefully considered. The region of skin that returns a detectable amount of diffusely reflected light varies considerably as a function of the illumination wavelength. For instance, for visible and very near infrared illumination, the short-wavelength illumination points may be laid out on a denser array than the long-wavelength points. It may be preferable for the embodiments that use swipe configurations to have the timing of the illumination and the image acquisition be sufficient for a relatively quick motion across the optically active region of the sensor. A modulated illumination method may advantageously be used for these types of sensors.

Thus, having described several embodiments, it will be recognized by those of skill in the art that various modifications, alternative constructions, and equivalents may be used without departing from the spirit of the invention. Accordingly,-the above description should not be taken as limiting the scope of the invention, which is defined in the following claims.

What is claimed is:

1. A method for determining a blood-alcohol level of an individual, the method comprising:
   receiving electromagnetic radiation emanating from tissue of the individual in response to propagation of electromagnetic radiation into the tissue of the individual;
   deriving a spatially distributed multispectral image from the received electromagnetic radiation;
   determining the blood-alcohol level from the multispectral image; and
   determining a biometric identification of the individual from the multispectral image.

2. The method recited in claim 1 wherein determining the blood-alcohol level from the multispectral image comprises determining amplitudes of the received electromagnetic radiation within a wavelength range of 2.1-2.5 µm.

3. The method recited in claim 1 wherein determining the blood-alcohol level from the multispectral image comprises determining amplitudes of the received electromagnetic radiation within a wavelength range of 2.2-2.4 µm.

4. The method recited in claim 1 wherein determining the blood-alcohol level from the multispectral image comprises determining amplitudes of the received electromagnetic radiation at one or more wavelength values approximately equal to values selected from the group consisting of 2.23 µm, 2.26 µm, 2.28 µm, 2.30 µm, 2.32 µm, 2.25 µm, and 2.38 µm.

5. The method recited in claim 1 wherein determining the blood-alcohol level from the multispectral image comprises determining amplitudes of the received electromagnetic radiation within a wavelength range of 1.5-1.9 µm.

6. The method recited in claim 1 wherein determining the blood-alcohol level from the multispectral image comprises determining amplitudes of the received electromagnetic radiation within a wavelength range of 1.6-1.8 µm.

7. The method recited in claim 1 wherein determining the blood-alcohol level from the multispectral image comprises determining amplitudes of the received electromagnetic radiation at one or more wavelength values approximately equal to values selected from the group consisting of 1.67 µm, 1.69 µm, 1.71 µm, 1.73 µm, 1.74 µm 1.76 µm and 1.78 µm.

8. The method recited in claim 1 wherein determining the blood-alcohol level from the multispectral image comprises correcting for optical drift of the received electromagnetic radiation.

9. The method recited in claim 8 wherein correcting for optical drift comprises measuring electromagnetic radiation emanating from a reference sample in response to propagation of electromagnetic radiation into the reference sample.

10. The method recited in claim 9 wherein the reference sample comprises a mixture of alcohol and water.

11. The method recited in claim 9 wherein measuring electromagnetic radiation emanating from the reference sample comprises measuring electromagnetic radiation within a wavelength range of 2.1-2.5 µm.

12. The method recited in claim 9 wherein measuring electromagnetic radiation emanating from the reference sample comprises measuring electromagnetic radiation within a wavelength range of 1.5-1.9 µm.

13. The method recited in claim 1 further comprising taking an action in response to a determination that the blood-alcohol level of the individual is outside a prescribed range.

14. The method recited in claim 13 wherein taking the action comprises prohibiting ignition of a motor vehicle.

15. The method recited in claim 1 further comprising making a biometric identification of the individual.

16. The method recited in claim 15 wherein making a biometric identification of the individual comprises comparing a spectral variation of the received electromagnetic radiation with a previously stored spectral variation.

17. The method recited in claim 15 further comprising taking an action in response to a combination of the determined blood-alcohol level and the biometric identification of the individual.

18. The method recited in claim 15 wherein:
   the electromagnetic radiation is propagated into the tissue of the individual at a skin site with a plurality of discrete wavelengths; and
   making the biometric identification of the individual comprise comparing the multispectral image with a database of multispectral images.

19. Apparatus for determining a blood-alcohol level of an individual, the apparatus comprising:
   a receiver adapted to receive electromagnetic radiation emanating from tissue of the individual in response to propagation of electromagnetic radiation into the tissue of the individual;
   a processor coupled with the receiver; and
   a computer-readable storage medium coupled with a processor, the computer-readable storage medium having a computer-readable program embodied therein for directing operation of the processor, the computer-readable program including:
   instructions for deriving a spatially distributed multispectral image from the received electromagnetic radiation;
   instructions for determining the blood-alcohol level from the multispectral image; and
   instructions for determining a biometric identification of the individual from the multispectral image.

20. The apparatus recited in claim 19 wherein the receiver comprises a sensor and an optical bandpass filter adapted to propagate light having a wavelength range of 2.1-2.5 µm.

21. The apparatus recited in claim 19 wherein the receiver comprises a plurality of sensors and a plurality of optical bandpass filters adapted to propagate light at a wavelength values approximately equal to values selected from the group consisting of 2.23 µm, 2.26 µm, 2.28 µm, 2.30 µm, 2.32 µm, 2.25 µm, and 2.38 µm.

22. The apparatus recited in claim 19 wherein the receiver comprises a sensor and an optical bandpass filter adapted to propagate light having a wavelength range of 1.5-1.9 µm.

23. The apparatus recited in claim 19 wherein the receiver comprises a plurality of sensors and a plurality of optical bandpass filters adapted to propagate light at a wavelength values approximately equal to values selected from the group consisting of 1.67 µm, 1.69 µm, 1.71 µm, 1.73 µm, 1.74 µm 1.76 µm and 1.78 µm.

24. The apparatus recited in claim 19 wherein the receiver comprises:
   a variable filter; and
   a detector array.

25. The apparatus recited in claim 24 wherein the detector array comprises a semiconductor detector array.

26. The apparatus recited in claim 24 wherein the detector array comprises a pyroelectric detector array.

27. The apparatus recited in claim 24 wherein the detector array comprises a bolometer detector array.

28. The apparatus recited in claim 19 further comprising a source of electromagnetic radiation adapted to propagate electromagnetic radiation into the tissue of the individual.

29. The apparatus recited in claim 28 wherein the source comprises a light-emitting diode.

30. The apparatus recited in claim 28 wherein the source comprises a laser diode.

31. The apparatus recited in claim 30 wherein the laser diode is tunable.

32. The apparatus recited in claim 19 wherein the computer-readable program further includes instructions for making a biometric identification of the individual from the received electromagnetic radiation.

33. The apparatus recited in claim 19 further comprising a biometric device adapted to make a biometric identification of the individual.

34. The apparatus recited in claim 33 wherein:
the electromagnetic radiation is propagated into the tissue of the individual at a skin site with a plurality of discrete wavelengths; and
the computer-readable program further includes instructions for comparing the multispectral image with a database of multispectral images.

35. The apparatus recited in claim 33 wherein the biometric identification is a nonoptical biometric identification.

36. A key fob comprising the apparatus recited in claim 19.

37. A motor vehicle comprising the apparatus recited in claim 19.

38. The method of claim 1, wherein determining the biometric identification occurs substantially contemporaneously with determining the blood-alcohol level.

39. The method of claim 1, wherein determining the biometric identification occurs in spatial proximity to determining the blood-alcohol level.

* * * * *